US009938410B2

(12) United States Patent
Bremberg et al.

(10) Patent No.: US 9,938,410 B2
(45) Date of Patent: Apr. 10, 2018

(54) RHODAMINE DYES AND CONJUGATES

(71) Applicant: PHARMACOPHOTONICS, INC., Indianapolis, IN (US)

(72) Inventors: Ulf J. Bremberg, Uppsala (SE); Erik Rinbgerg, Uppsala (SE); Wei Berts, Enkoping (SE); Anthony De Belder, Uppsala (SE); James S. Strickland, Zionsville, IN (US)

(73) Assignee: PHARMACOPHOTONICS, INC., Indianapolis, IN (US)

( * ) Notice: Subject to any disclaimer, the term of this patent is extended or adjusted under 35 U.S.C. 154(b) by 0 days.

(21) Appl. No.: 14/922,810

(22) Filed: Oct. 26, 2015

(65) Prior Publication Data
US 2016/0208101 A1 Jul. 21, 2016

Related U.S. Application Data

(63) Continuation of application No. 14/283,403, filed on May 21, 2014, now Pat. No. 9,169,398, which is a continuation of application No. 13/638,744, filed as application No. PCT/US2011/030999 on Apr. 1, 2011, now Pat. No. 8,809,531.

(60) Provisional application No. 61/320,571, filed on Apr. 2, 2010.

(51) Int. Cl.
*C09B 11/24* (2006.01)
*C09B 5/00* (2006.01)
*A61K 49/00* (2006.01)

(52) U.S. Cl.
CPC .......... *C09B 11/24* (2013.01); *A61K 49/0041* (2013.01); *A61K 49/0054* (2013.01); *C09B 5/00* (2013.01)

(58) Field of Classification Search
CPC ....... C09B 11/24; C09B 5/00; A61K 40/0041; A61K 40/0054
See application file for complete search history.

(56) References Cited

U.S. PATENT DOCUMENTS

| 5,459,268 A * | 10/1995 | Haugland ............... C09B 11/12 546/37 |
| 5,614,386 A * | 3/1997 | Metzker ................. C07H 21/00 435/5 |
| 6,750,357 B1 | 6/2004 | Chiarello et al. |
| 7,045,319 B2 * | 5/2006 | Hanna .................. C12Q 1/6858 435/6.12 |
| 2003/0010438 A1 | 1/2003 | Tharpe et al. |
| 2006/0269479 A1 | 11/2006 | Colton et al. |
| 2012/0029528 A1 | 2/2012 | Macdonald et al. |

FOREIGN PATENT DOCUMENTS

| EP | 0603160 A2 | 6/1994 |
| FR | 2889060 B1 | 2/2007 |
| JP | 2004/061947 * | 2/2004 |
| JP | 2006525022 A | 11/2006 |
| JP | 2009513753 A | 4/2009 |
| JP | 2013523964 A | 6/2013 |
| WO | 00/030632 A1 | 6/2000 |
| WO | W003/002715 A2 | 1/2003 |
| WO | 2004085386 A2 | 10/2004 |
| WO | 2007039502 A2 | 4/2007 |
| WO | W02007/039502 A2 | 4/2007 |
| WO | 2009046165 A1 | 4/2009 |

OTHER PUBLICATIONS

Translation of Office Action in Japanese Patent Application No. 2014-222269—dated Nov. 24, 2015.
Mier Walter. Bioorganic & Medicinal Chemistry, 2002, VIO NS, P2543-2552.
Communication of the European Patent Office (EPO) under Rule 164(2)(a) EPC for European patent application No. 11714475.8, dated Aug. 4, 2017.
Examiner's Report for Canadian Patent Application No. 2,794,678, dated Jun. 8, 2017.

\* cited by examiner

*Primary Examiner* — Timothy R Rozof
(74) *Attorney, Agent, or Firm* — Burns & Levinson LLP; Bruce D. Jobse; Janine M. Susan

(57) ABSTRACT

The present invention relates generally to novel rhodamine dyes which upon conjugation with another molecule form single isomeric conjugation products. These novel rhodamine dyes contain only one single functional group on the rhodomine molecule for conjugation so that their conjugation products are single isomeric conjugation products.

10 Claims, 6 Drawing Sheets

Single isomer
(present invention)

RHODAMINE DYES AND CONJUGATES

CROSS-REFERENCE TO RELATED APPLICATION

The present application is a continuation of U.S. patent application Ser. No. 14/283,403, filed May 21, 2014, entitled RHODAMINE DYES AND CONJUGATES, which in turn is a continuation of U.S. patent application Ser. No. 13/638,744, now U.S. Pat. No. 8,809,531, which in turn is a U.S. national stage application under 35 U.S.C. 371 of PCT/US11/30999, filed Apr. 1, 2011, which in turn claims the benefit of U.S. Provisional Patent Application No. 61/320,571, filed Apr. 2, 2010, the contents of which are incorporated herein by reference in their entirety for all purposes.

FEDERALLY SPONSORED RESEARCH OR DEVELOPMENT

None.

FIELD OF THE INVENTION

The present invention relates generally to novel rhodamine dyes which upon conjugation with another molecule to form single isomeric conjugation products.

BACKGROUND OF THE INVENTION

Rhodamine dyes fluoresce and have been used extensively in research, both as free dye and as conjugates to larger molecules, e.g. proteins and antibodies (Lee S, McAuliffe D J, Kodama T, Doukas A G, In vivo transdermal delivery using a shock tube, Shock Waves (2000) 10:307-307; Janson L W, Ragsdale K, Luby-Phelps K, Mechanism and size cutoff for steric exclusion from actin-rich cytoplasmic domains., Biophys J (1996) 71:1228-1234; Pu R, Robinson K R, Cytoplasmic calcium gradients and calmodulin in the early development of the fucoid alga Pelvetia compressa., J Cell Sci (1998) 111 (Pt 21):3197-3207; Nishiya T, Kajita E, Horinouchi T, Nishinioto A, Miwa S, Distinct roles of TIR and non-TIR regions in the subcellular localization and signaling properties of MyD88, FEBS Lett (2007) 581:3223-3229; Tanner G A, Sandoval R M, Dunn K W, Two-photon in vivo microscopy of sulfonefluorescein secretion in normal and cystic rat kidneys, Am J Physiol Renal Physiol (2004) 286:F152-F160).

Structurally, rhodamine is a family of related polycyclic flurone dyes with a xanthene core.

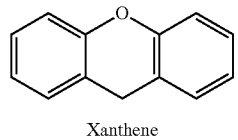 [SMILES: c1ccc2c(c1)Cc1ccccc1O2]

Xanthene

The general structure of rhodamine is as follows:

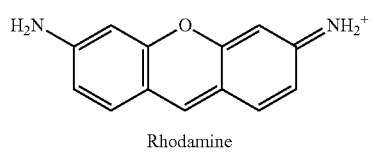

Rhodamine

The amines of rhodamine can be primary amines, secondary amines or tertiary amines.

One of the commonly used fluorescent rhodamine dye is sulforhodamine 101 which contains a julolidine structure element:

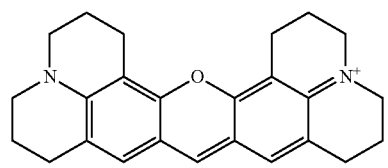

Julolidine structure element

Sulforhodamine 101 contains bi-functional sulfonyl groups as shown below:

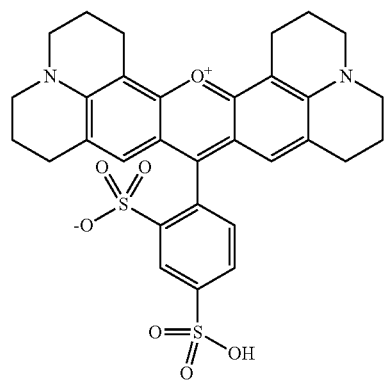

Sulforhodamine 101

Sulfonylrhodamine 101 has been used in neurophysiological experiments which comprise calcium imaging methods as well as a counterstaining of astrocytes (Nimmerjahn, A., Kirchhoff, F., Kerr, J. N., Helmchen, F., Sulforhodamine 101 as a specific marker of astroglia in the neocortex in vivo, Nature Methods (2004) 1:31-7).

A sulfonyl chloride derivative of sulforhodamine 101 is sold by Sigma Aldrich, Inc. (St. Louis, Mo.) under the trademark. Texas Red®. It is used for conjugation with a number of functional groups, especially with primary amities. Texas Red® fluoresces at about 615 nm with a peak absorption at 589 nm. Texas Red® is typically available as a mixture of two monosulfonyl chlorides with the $SO_3$ and $SO_2Cl$ groups exchangeable as shown below:

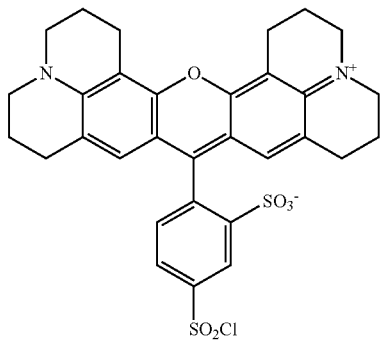

or

-continued

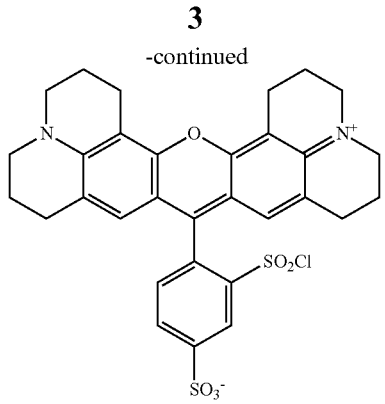

Other rhodamine derivatives have also been disclosed, such as in PCT Int. Appl. (2009), WO 2009108905 A2 2009090; U.S. Pat. Appl. Publ. No. 2004054162 A1 20040318; U.S. Pat. No. 5,728,529; U.S. Pat. No. 5,686,261; PCT Int. Appl. (1997), WO 9700967 A1 19970109; U.K. Pat. Appl. (1995), GB 2283744 A 19950517; and by Kim etl al. (Kim, T. G.; Castro, J. C.; Loudet, A.; Jiao, J. G.-S.; Hochstrasser, R. M.; Burgess, K.; Topp, M. R., Journal of Physical Chemistry A (2006), 110(1), 20-27).

Although several publications show the possibility of using bi-functional rhodamine dyes for conjugation, e.g. by selective reaction of one of the sulfonyl chloride groups in Texas Red® (Titus J A, Haugland R, Sharrow S O, Segal D M, Texas Red, a hydrophilic, red-emitting fluorophore for use with fluorescein in dual parameter flow microfluorometric and fluorescence microscopic studies, J. Immunol. Methods (1982) 50 (2): 193-204), the possibility of dual reactivity gives difficulties in establishing a reliable process yielding a single isomer product only, which is shown in FIG. 1 in which a bi-functional rhodamine dye with two sulfonyl groups reacting with a primary amine to form two conjugation isomeric products. Two isomeric structures instead of only one in a process gives two major disadvantages: 1) the ratio of isomers changes from batch to batch with product impacting effects, and 2) the regulatory requirements (toxicity data, stability, characterization, etc) will be doubled to cover two substances instead of one.

The present invention circumvents these difficulties by using novel mono-functional derivatives of rhodamine dye with only one single functional group on the rhodomine molecule for conjugation so that their conjugation products are single isomeric conjugation products.

These and other aspects and attributes of the present invention will be discussed with reference to the following drawings and accompanying specification.

DETAILED DESCRIPTION OF THE INVENTION

While this invention is susceptible of embodiments in many different forms, there are specific embodiments which will be described herein in detail with the understanding that the present disclosure is to be considered as an exemplification of the principles of the invention and is not intended to limit the invention to the specific embodiments illustrated.

It will be understood that the chemical structures that are used to define compounds of the present invention are each representations of one of the possible resonance structures that each given structures can be represented by. Further, it will be understood that by definition, resonance structures are merely a graphical representation used by those of skill in the art to represent electron derealization, and that the present disclosure are not limited in any way by showing one particular resonance, structure for a given structure.

It will also be understood that the chemical structures that are used to define compounds of the present invention also include their structures in their respective salt forms.

The present invention relates generally to novel rhodamine dyes which upon conjugation with another molecule to form single isomeric conjugation products.

Figure 1:
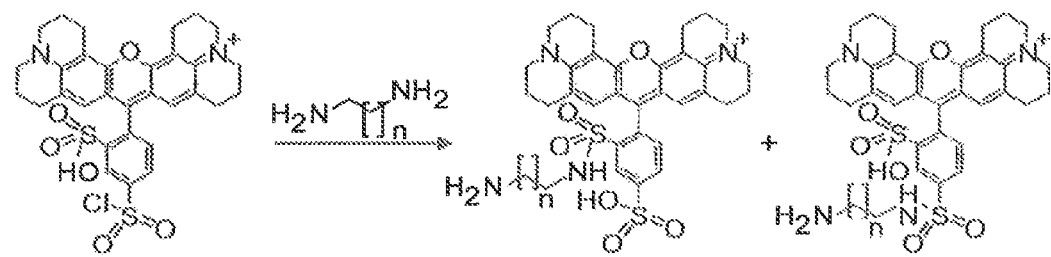
FIG. 1 shows the conjugation of a bi-functional rhodamine dye with a macromolecule to form two isomeric conjugation products.

Although several publications show the possibility of using bi-functional rhodamine dyes for conjugation, e.g. by selective reaction of one of the sulfonyl chloride groups in Texas Red® (Titus J A, Haugland R, Sharrow S O, Segal D M, Texas Red, a hydrophilic, red-emitting fluorophore for use with fluorescein in dual parameter flow microfluorometric and fluorescence microscopic studies, J. Immunol. Methods (1982) 50 (2): 193-204), the possibility of dual reactivity gives difficulties in establishing a reliable process yielding a single isomer product only. As shown in FIG. 1, a bi-functional rhodamine dye with two sulfonyl groups reacts with a primary amine to form two conjugation isomeric products. Two isomeric structures instead of only one in a process gives two major disadvantages: 1) the ratio of isomers changes from batch to batch with product impacting effects, and 2) the regulatory requirements (toxicity data, stability, characterization, etc) will be doubled, to cover two substances instead of one.

Figure 2:
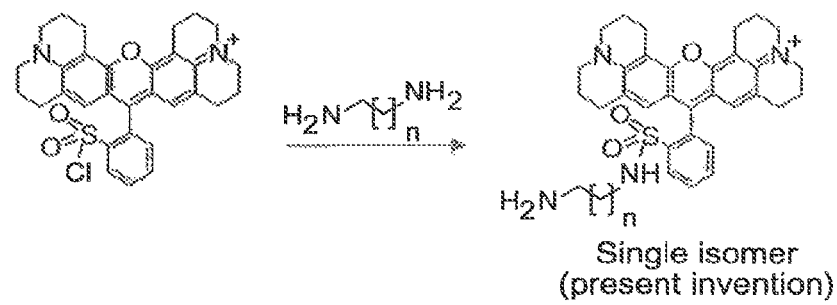
FIG. 2 shows the conjugation of a mono-functional rhodamine dye with a macromolecule to form only one single isomeric conjugation product.

The present invention circumvents these difficulties by using novel mono-functional derivatives of rhodamine dye with only one single functional group on the rhodomine molecule for conjugation so that their conjugation products are single isomeric conjugation products as illustrated in FIG. 2. FIG. 2 illustrates an example of the present invention in which a rohodamine derivative with a single sulfonyl group reacts with a primary amine to form only a single isomeric conjugation product. What is meant by a "functional group" is that the group is suitable for conjugation. The functional group suitable for conjugation is reactive to another molecule, such as a macromolecule, to form a conjugate via a covalent bond. A rhodamine derivative containing only one "functional group" is known as mono-functionalized or a mono-functional derivative (such as the mono-sulfonyl rhodamine in FIG. 2) which differentiates from rohodamine derivatives containing more than one "functional groups" such as sulfonylrhodamine 101 or Texas Red®. Examples of functional groups suitable for conjugation include but are not limited to amines, isocyanates, isothiocyanates, thiols, carboxylic acids and the like. "Functionalized" herein means that the rhodamine derivative has been derivatised to contain a "functional group". An example is "amino-functionalized" meaning that the functional group contains the reactive amino group.

Figure 3:
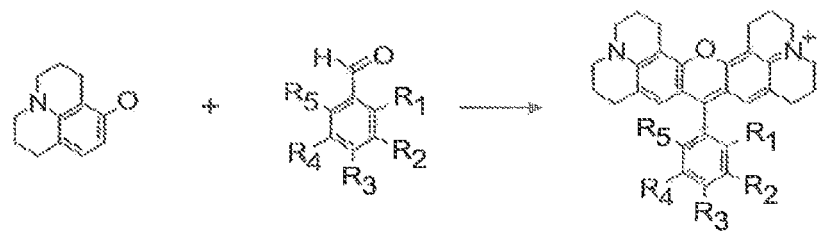
FIG. 3 shows the formation of the novel rhodamine dye of the present invention from 8-hydroxyjulolidine (2 equivalents) and a substituted benzaldehyde (1 equivalent) wherein $R_1$, $R_2$, $R_3$, $R_4$ and $R_5$ can be a H or any group.

In an embodiment, the novel rhodamine dyes of the present invention have a general structure of:

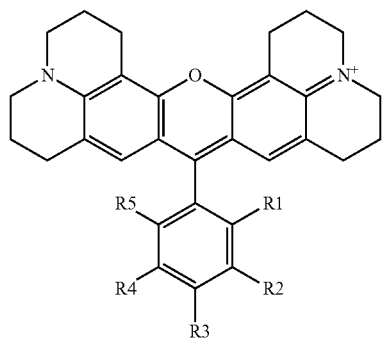

wherein R1, R2, R3, R4 and R5 can be a H or any group. However, among R1, R2, R3, R4 and R5, only one of these groups can have a "functional group" so that the rhodamine dye has only one single "functional group" capable of conjugation with, another molecule, such as a macromolecule, to form a single conjugation isomeric product. This general structure can be formed by reacting 8-hydroxyjulodine (2 equivalents) with a substituted benzaldehyde (1 equivalent) as shown in FIG. 3. The 8-hydroxyjulodine and the substituted benzaldehyde can be mixed with 60% aqueous sulfuric acid (11.1 mL/mmol benzaldehyde) and stirred at 150° C. for 24 h under air atmosphere. The reaction mixture can be added to ice (28 g/mmol benzaldehyde), after which 60% NaOH can be carefully added to pH 6-7 to precipitate the crude product. The crude product can be extracted between dichloromethane (DCM) and water. The organic phase can be separated, and washed with brine. The organic solvent can be removed and the final product dried by evaporating with ethanol and toluene 5 times to give the crude product. Detailed methods for preparing specific examples of the rhodamine dyes of the present invention are described in Examples below.

Some examples of general structures of mono-functional rhodamine derivatives suitable to form single isomeric conjugation products are shown below with the general formula of 2-sulforhodamine:

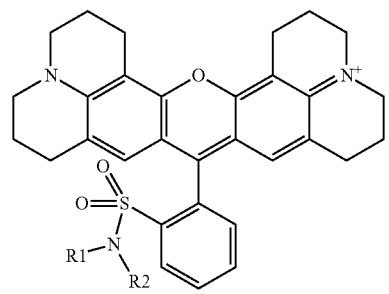

or the general formula of 4-carboxrhodamine:

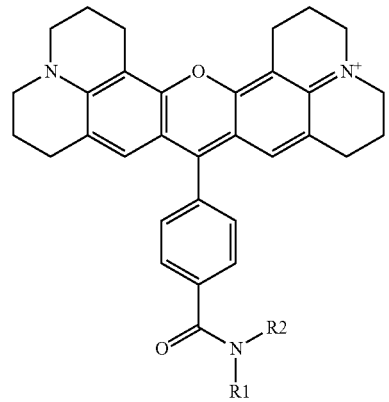

or the general formula of 3-carboxrhodamine:

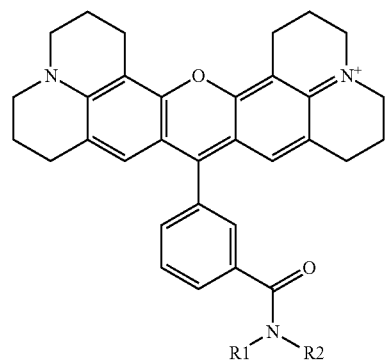

or the general formula of 4-arylrhodamine:

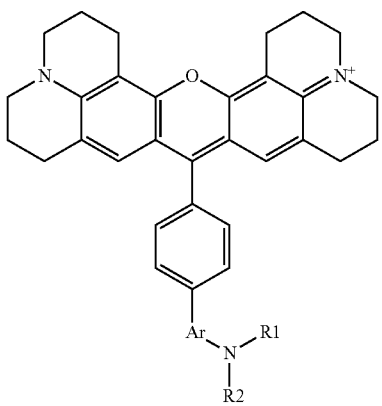

wherein for all the above 4 general formulas, Ar is an aryl group, and R1 and/or R2 form a spacer with a single functional group on either R1 or R2 suitable for conjugation with another molecule, wherein the spacer can be, but is not limited to, hydrogen, alkyl, aryl, amide, alkyl sulfonamide, alkyl ether, alkyl amide and the like, or a combination thereof. The alkyl groups mentioned above preferably have a carbon chain length of from 1 to 20. R1 and R2 can also be connected to form a cyclic structure, such as but not limited to the structures shown below:

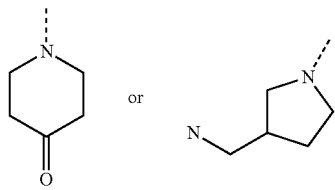

Although the examples shown above show that the sulfo-group is in the 2 position, the carbox-group is in the 3 or 4 position and the aryl-group is in the 4 position, it should be noted that these and other groups containing the "functional" group can be in the 2, 3 or 4 position. The examples below (Examples 4-24) illustrate the synthesis of some of the members belonging to the groups shown above. However, the synthesis of other related compounds with the sulfo-, carbox-, aryl- or any other group positioning at any desired position in the novel rhodamine dye of the present invention should be obvious to those skilled in the art with the illustrations from the Examples.

In a preferred embodiment, the novel rhodamine derivatives are in the form of a salt, such as but are not limited to trifluoroacetate, chloride, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate and p-toluenesulfonate. In a further preferred embodiment, the salt is trifluoroacetate or chloride. In yet another preferred embodiment, the salt is a pharmaceutically acceptable salt.

Figure 4:
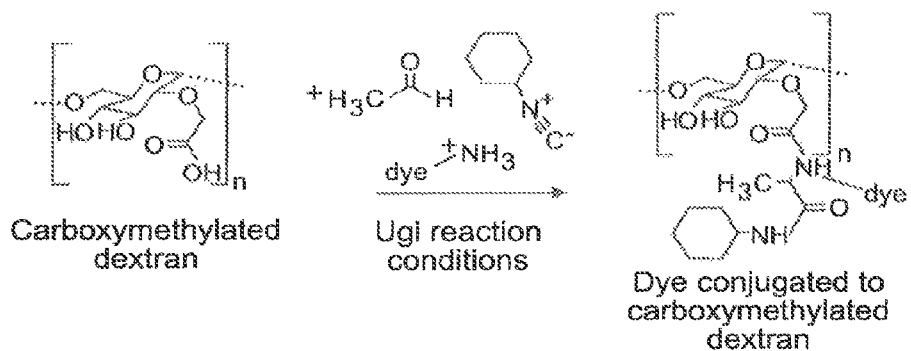
FIG. 4 shows the general conjugation reaction under the Ugi reaction conditions between a rhodamine dye with a mono-functional group and a macromolecule.
Figure 5:
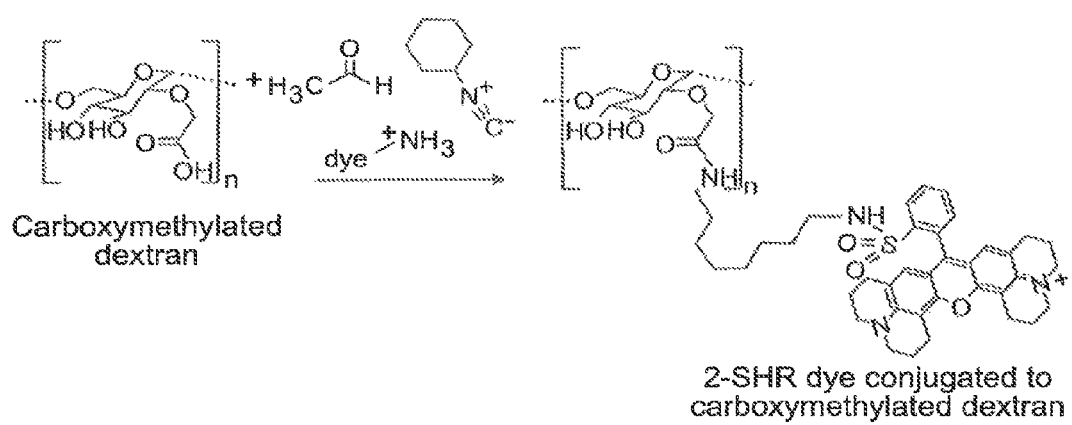
FIG. 5 is an example of conjugation with the Ugi reaction of a mono-functional 2-sulforhodamine (2-SHR) dye having a single functional primary amino group with carboxmethylated dextran to form a single isomeric conjugation product.

One of the applications for these novel mono-functional rhodamine derivatives is their ability to conjugate to another molecule, such as a macromolecule. The molecule, such as a macromolecule, when conjugated to the rhodamine dye can be easily detectable and/or quantifiable. Commonly used macromolecules herein include but are not limited to polymers, proteins (such as antibodies), dextrans, celluloses, carbohydrates, lipids, nucleic acids (such as DNA and RNA) and the like. Conjugation of rhodamine dyes with macromolecules and their applications are well known to those skilled in the art, and has been described in details in the scientific literature, such as disclosed by Titus et al. (Titus J A, Haugland R, Sharrow S O, Segal D M, Texas Red, a hydrophilic, red-emitting fluorophore for use with fluorescein in dual parameter flow micro fluorometric and fluorescence microscopic, studies, J. Immunol. Methods 50 (1982) 2:193-204) and by Haugland et al. in U.S. Pat. No. 5,798,276. Conjugates of rhodamine with macromolecules such as antibodies are readily commercially available such as Human IgG antibody conjugated with rhodamine from Abcam (Cambridge, Mass.) and various proteins conjugated with rhodamine dyes from Sigma Aldrich (St. Louis, Mo.). Any synthetic methodology that creates a covalent bond between the functional group of the dye and the macromolecule can be used for conjugation. The general conjugation reaction between the rhodamine dye and a macromolecule under the Ugi reaction conditions is illustrated in FIG. 4, exemplified by the conjugation of the amino-functionalized sulfonamide dye (Compound 1 shown in Example 6) to carboxymethylated dextran with the Ugi reaction, as shown in FIG. 5.

To illustrate the invention, a number of structures suitable for conjugation have been synthesized (Compounds 1-19) which are shown in the Examples 6-24 below. Experimental details of further examples of conjugations are shown with Examples 25-28 below, using dyes from the synthesized examples (Compound 18, Compound 3, Compound 15 and Compound 16) conjugating with carboxymethylated-dextran (CM-dextran).

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

EXAMPLES

Solvents and reagents are used as received from Labscan (Gliwice, Poland) and Sigma Aldrich (St. Louis, Mo.), respectively. A Liquid Chromatography-Mass Spectroscopy (LCMS) system from Agilent Technologies (Santa Clara, Calif.) is used, which consists of a G1379B degasser, a G1312A binary pump, a G1329A autoinjector, a G1316A column oven, a G1365B UV-Vis detector (used to detect absorbance maxima) and a 6110 Quadrupole MS detector. High Performance Liquid Chromatography (HPLC) purities are measured with an ACE-C8 column (50×4.6 mm) held at 35° C. and eluted with 10-97% acetonitrile in 0.1% trifluoral acetic acid (TEA) over a 3 minute gradient.

The compounds in the following Examples are named based on Marvin Sketch 5.2.6, using Preferred IUPAC naming settings for structure naming. However, other nomenclature systems can be employed to name these compounds.

Example 1: Preparation Intermediate 1

The following compound is prepared:

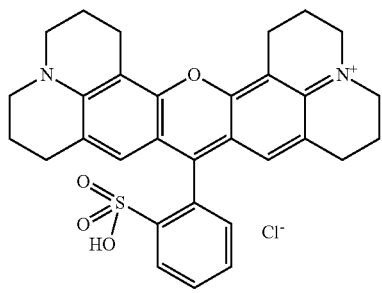 [SMILES: O=S(=O)(O)c1ccccc1C1=c2cc3c4c(c2Oc2c1cc1c5c2CCCN5CCC1)CCC[N+]=4CCC3 ; [Cl-]]

Intermediate 1

A reaction mixture of 8-hydroxyjulolidine (1.1 g, 5.8 mmol) and sodium 2-formylbenzene-1-sulfonate (0.6 g, 2.9 mmol) in 60% aqueous $H_2SO_4$ (10 mL) is stirred at 150° C. under an air atmosphere for 2 hours, after which time the starting materials have converted to the expecting product completely. pH of the reaction is adjusted to about 7 with aqueous 60% of NaOH, in which procedure the expecting product is precipitated. The precipitation is filtered and washed with toluene (3×50 mL) and dried under vacuum. The crude product is dissolved in warm ethanol (EtOH) and filtered. Insoluble solid is discarded, and the filtrate is evaporated in vacuo with toluene (3×50 ml), and 1.1 g title molecule is obtained with 90% HPLC purity and 73% yield.

Example 2: Preparation of Intermediate 2

The following compound is prepared:

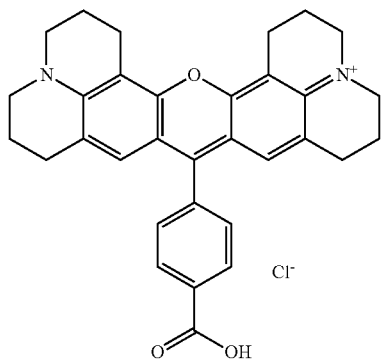 [SMILES: O=C(O)c1ccc(C2=c3cc4c5c(c3Oc3c2cc2c6c3CCCN6CCC2)CCC[N+]=5CCC4)cc1 ; [Cl-]]

Intermediate 2

8-Hydroxyjulolidine (1.4 g, 7.2 mmol) and 4-formyl benzoic acid (500 mg, 3.6 mmol) are mixed with 60% aqueous sulfuric (40 mL) and stirred at 150° C. for 24 hours under air atmosphere. The reaction mixture is added to ice (100 g), after which 60% NaOH is carefully added to pH 6-7, precipitating the crude product. The crude product is extracted between dichloromethane (DCM) and water. The organic phase is separated, and washed with brine. The organic solvent is removed and the final products are dried by evaporating with EtOH and toluene 5 times to yield 1.1 g product (61% yield). Purity as determined by HPLC is 100%. MS (ESI) [M+]=491.

Example 3: Preparation of Intermediate 3

The following compound is prepared:

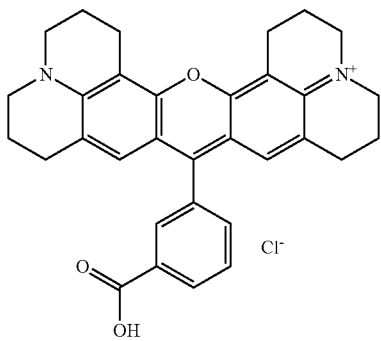 [SMILES: O=C(O)c1cccc(C2=c3cc4c5c(c3Oc3c2cc2c6c3CCCN6CCC2)CCC[N+]=5CCC4)c1 ; [Cl-]]

Intermediate 3

8-Hydroxyjulolidine (1.4 g, 7.2 mmol) and 3-formyl benzoic acid (500 mg, 3.6 mmol) are mixed with 60% aqueous sulfuric (40 mL) and stirred at 150° C. for 24 hours under air atmosphere. The reaction mixture is added to ice (100 g), after which 60% NaOH is carefully added to pH 6-7, precipitating the crude product. The crude product is extracted between DCM and water. The organic phase is separated, and washed with brine. The organic solvent is removed and the final products are dried by evaporating with EtOH and toluene 5 times to yield 1.7 g 3-acid product (94% yield). Purity as determined by HPLC is 95%. MS (ESI) [M+]=491.

Example 4: Preparation of Intermediate 4

The following compound is prepared:

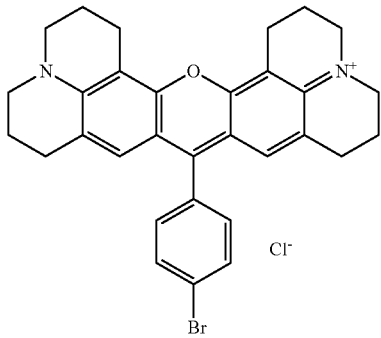 [SMILES: Brc1ccc(C2=c3cc4c5c(c3Oc3c2cc2c6c3CCCN6CCC2)CCC[N+]=5CCC4)cc1 ; [Cl-]]

Intermediate 4

8-Hydroxyjulolidine (1.4 g, 7.2 mmol) and 4-bromobenzaldehyde (670 mg, 3.6 mmol) are mixed with 60% aqueous sulfuric (40 mL) and stirred at 150° C. for 24 hours under air atmosphere. The reaction mixture is added to ice (100 g), after which 60% NaOH is carefully added to pH 6-7, precipitating the crude product and dried under vacuum overnight to 1.12 g black solid. The crude product is dissolved in 90/10 CHCl$_3$/methanol (5 mL) and applied on to a column of silica (35×100 mm) and eluted with 10-18% methanol in CHCl$_3$. Pure fractions are pooled and the solvent is evaporated at reduced pressure to 448 mg product.

Example 5: Preparation of Intermediate 5

The following compound is prepared:

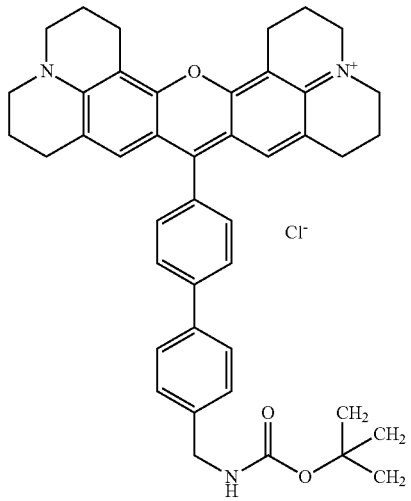 [SMILES: CC(C)(C)OC(=O)NCc1ccc(-c2ccc(C3=c4cc5c6c(c4Oc4c3cc3c7c4CCCN7CCC3)CCC[N+]=6CCC5)cc2)cc1 ; [Cl-]]

Intermediate 5

Intermediate 4 prepared as described in Example 4 (236 mg, 0.45 mmol) and tert-butyl N-{[4-(dihydroxyboranyl) phenyl]methyl}carbamate (225 mg, 0.90 mmol) are transferred to a 50 mL flask with ethanol and 2M K$_2$CO$_3$ aqueous solution (672 µL, 1.34 mmol) added. The reaction mixture is briefly degassed and [1,1'-bis(diphenylphosphino)ferrocene] dichloropalladium(II). DCM (18 mg, 0.022 mmol)) is added, degassing again and stirred under nitrogen at room temperature. After 50 minutes of stirring, add more [1,1'-bis(diphenylphosphino)ferrocene]dichloropalladium(II). DCM (13 mg, 0.016 mmol) is added and the mixture heated to 65° C. for 1 hour. This is followed by evaporation and dissolution in DCM, addition of 4 g silica and evaporation and silica chromatography through a 12×2.5 cm column, packed with DCM, eluted with 5-20% methanol (MeOH) in DCM and evaporation of pure fraction gave 236 mg golden brown sticky solid with 90% HPLC purity.

Example 6: Preparation of a 2-sulforhodamine trifluoroacetate (Compound 1)

The following compound is prepared:

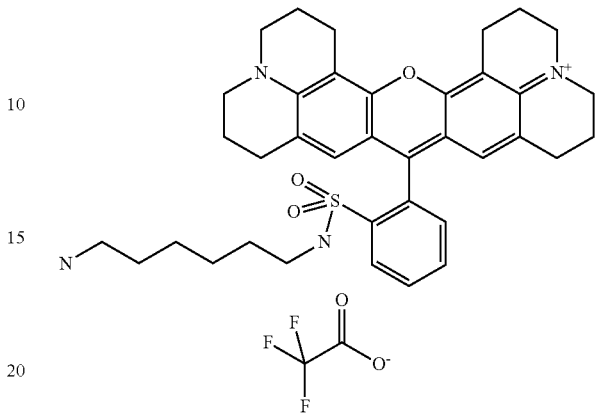

Compound 1

Compound 1 is 16-{2-[(6-aminohexyl)sulfamoyl]phenyl}-3-oxa-9λ$^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; 2,2,2-trifluoroacetate according to the nomenclature system that we use and is prepared as follows. Intermediate 1 (0.66 mmol, 350 mg) is dissolved in DCM (10 mL) and a drop of dimethylformamide (DMF). Oxalyl-chloride (3.98 mmol, 500 mg) is added and the reaction mixture is stirred at room temperature for one hour. An evolution of gas is immediately noted. The solvent is evaporated, mixed with toluene (10 mL) and reevaporated, the residue dissolved in DCM (12 mL), cooled in an ice bath, and divided into two equal portions. One portion is carefully (under 5 minutes) added to an ice cold solution of hexamethylenediamine (1.06 mmol, 120 mg) in DCM (5 mL) and triethylamine (0.40 mmol, 40 mg) in DCM (5 mL). The dark bluish solutions switch immediately to dark red. Exaction completes within 30 minutes. A part of the crude mixture is purified on preparative HPLC, ACE-C8 column with a methanol gradient in 0.1% TFA in water to give 58 mg (24%) of product as a dark blue copper shimmering glass. Purity as determined by HPLC is 100%. MS (ESI) [M+]= 625. Absorbance max is 586 nm.

Example 7: Preparation of a 2-sulforhodamine trifluoroacetate (Compound 2)

The following compound is prepared:

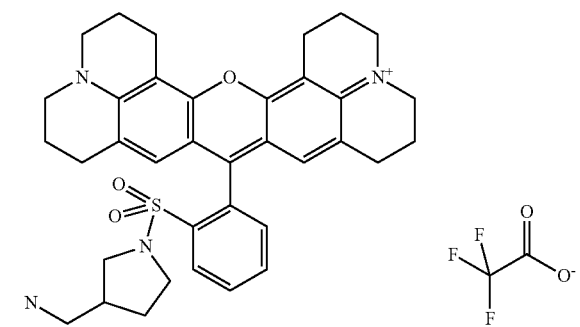 [SMILES: NCC1CCN(S(=O)(=O)c2ccccc2C2=c3cc4c5c(c3Oc3c2cc2c6c3CCCN6CCC2)CCC[N+]=5CCC4)C1 ; O=C([O-])C(F)(F)F]

Compound 2

Compound 2 is 16-{2-[3-(aminomethyl)pyrrolidine-1-sulfonyl]phenyl}-3-oxa-9λ$^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; 2,2,2-trifluoroacetate according to the nomenclature system that we use and is prepared as follows. Intermediate 1 (0.66 mmol, 350 mg) is dissolved in DCM (10 mL) and a drop of DMT. Oxalylchloride (3.98 mmol, 500 mg) is added and the reaction mixture is stirred at room temperature for one hour. An evolution of gas is immediately noted. The solvent is evaporated, mixed with toluene (10 mL) and reevaporated, the residue dissolved in DCM (12 mL), cooled in an ice bath, divided into two equal portions. One portion is carefully (under 5 minutes) added to an ice cold solution of tert-butyl N-(pyrrolidin-3-ylmethyl)carbamate (1.06 mmol, 90 mg) in DCM (5 mL) and triethylamine (0.40 mmol, 40 mg) in DCM (5 mL). The dark bluish solutions switch immediately to dark red. Reaction completes within 30 minutes. TFA is added (1 mL in ca 2 mL of DCM), completes deprotection in one hour. A part of the crude is purified on preparative HPLC, ACE-C8 column with a methanol gradient in 0.1% TFA in water to give 95 mg (39%) as a dark blue copper shimmering glass. Purity as determined by HPLC is 100%. MS (ESI) [M+]=605. Absorbance max is 590 nm.

Example 8: Preparation of a 4-carboxrhodamine trifluoroaceate (Compound 3)

The following compound is prepared:

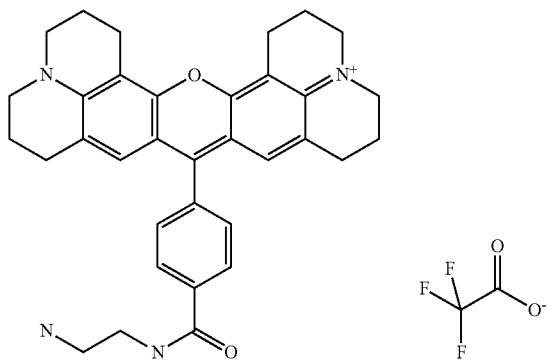 [SMILES: NCCNC(=O)c1ccc(C2=c3cc4c5c(c3Oc3c2cc2c6c3CCCN6CCC2)CCC[N+]=5CCC4)cc1 ; O=C([O-])C(F)(F)F]

Compound 3

Compound 3 is 16-{4-[(2-aminoethyl)carbamoyl]phenyl}-3-oxa-9λ$^5$,23-diazaheptacyclo[17.7.1.1$^{5,9}$.0$^{2,17}$.0$^{4,15}$.0$^{23,27}$.0$^{13,28}$]octacosa-1(27),2(17)4,9(28),13,15,18-heptaen-9-ylium; 2,2,2-trifluoroacetate according to the nomenclature system that we use and is prepared as follows. Intermediate-2 (1.50 mg, 0.31 mmol) is dissolved in DMF-CH$_3$CN (1-4, 7 mL). Triethylamine (94 mg, 0.93 mmol) and 2,4,6-tripropyl-1,3,5,2,4,6-trioxatriphosphorinane-2,4,6-trioxide solution in ethyl acetate (592 μL, 0.93 mmol) are added and the mixture stirred at room temperature for 15 minutes. A ⅙-part is taken out and added to 1,2-diaminoethane (19 mg, 0.31 mmol) and the reaction mixture stirred at room temperature for 1.5 hours. Purification is preformed on preparative HPLC, ACE-C8 column with a methanol gradient in 0.1% TFA in water to give 24 mg (72%) as a dark blue black glass. Purity as determined by HPLC is 93%. MS (ESI) [M+]=533. Absorbance max is 586 nm.

Example 9: Preparation of a 4-carboxrhodamine trifluoroaceate (Compound 4)

The following compound is prepared:

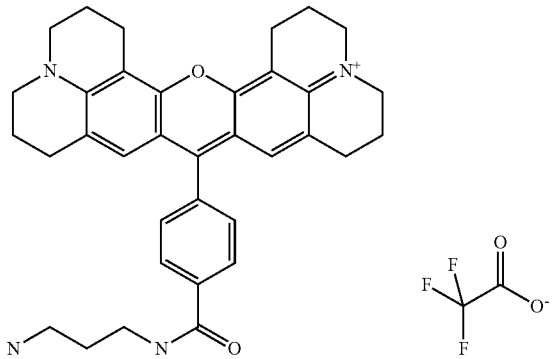 [SMILES: NCCCNC(=O)c1ccc(C2=c3cc4c5c(c3Oc3c2cc2c6c3CCCN6CCC2)CCC[N+]=5CCC4)cc1 ; O=C([O-])C(F)(F)F]

Compound 4

Compound 4 is 16-{4-[(3-aminopropyl)carbamoyl]phenyl}-3-oxa-9λ$^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; 2,2,2-trifluoroacetate according to the nomenclature system that we use and is prepared using the same procedure as used for preparing Compound 3, but with 1,3-diaminopropane replacing 1,2-diaminoethane (23 mg, 0.31 mmol) to obtain 25 mg (73% yield) product. Purity as determined by HPLC is 100%. MS (ESI) [M+]=547. Absorbance max is 584 nm.

Example 10: Preparation of a 4-carboxrhodamine trifluoroaceate (Compound 5)

The following compound is prepared:

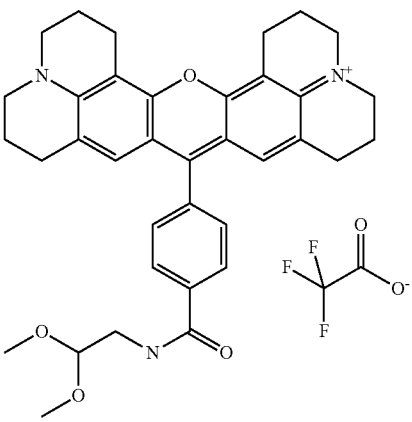 [SMILES: COC(CNC(=O)c1ccc(C2=c3cc4c5c(c3Oc3c2cc2c6c3CCCN6CCC2)CCC[N+]=5CCC4)cc1)OC ; O=C([O-])C(F)(F)F]

Compound 5

Compound 5 is 16-{4-[(2,2-dimethoxyethyl)carbamoyl]phenyl}-3-oxa-9λ$^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18- heptaen-9-ylium; 2,2,2-trifluoroacetate according to the nomenclature system that we use and is prepared using the same procedure as used for preparing Compound 3, but with 2,2-dimethoxyethan-1-amine replacing 1,2-diaminoethane (33 mg, 0.31 mmol) to obtain 26 mg (73% yield) product. Purity as determined by HPLC is 100%. MS (ESI) [M+]= 578. Absorbance max is 584 nm.

Example 11: Preparation of a 4-carboxrhodamine trifluoroaceate (Compound 6)

The following compound is prepared:

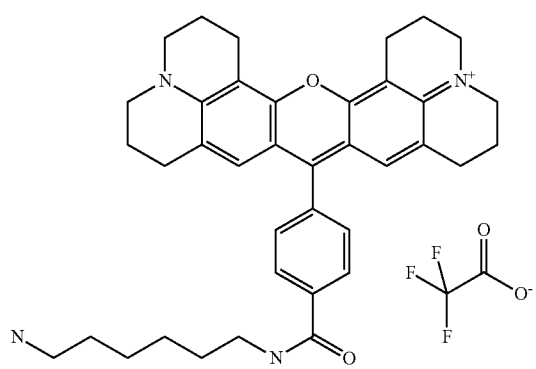 [SMILES: NCCCCCCNC(=O)c1ccc(C2=c3cc4c5c(c3Oc3c2cc2c6c3CCCN6CCC2)CCC[N+]=5CCC4)cc1 ; O=C([O-])C(F)(F)F]

Compound 6

Compound 6 is 16-{4-[(6-aminohexyl)carbamoyl]phenyl}-3-oxa-9$\lambda^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),3,15,18-heptaen-9-ylium; 2,2,2-trifluoroacetate according to the nomenclature system that we use and is prepared using the same procedure as used for preparing Compound 3, but with 1,6-diaminohexane replacing 1,2-diaminoethane (36 mg, 0.31 mmol) to obtain 32 mg (88% yield) product. Purity as determined by HPLC is 100%, MS (ESI) [M+]=589. Absorbance max is 586 nm.

Example 12: Preparation of a 4-carboxrhodamine trifluoroaceate (Compound 7)

The following compound is prepared:

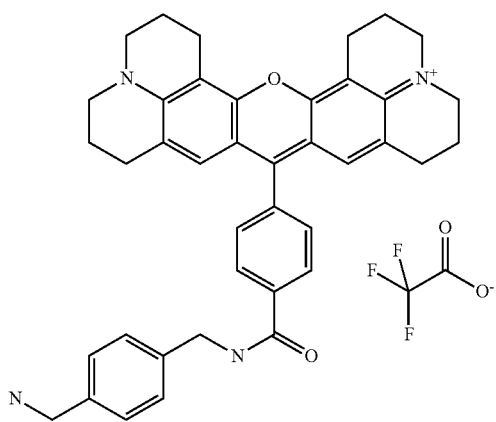 [SMILES: NCc1ccc(CNC(=O)c2ccc(C3=c4cc5c6c(c4Oc4c3cc3c7c4CCCN7CCC3)CCC[N+]=6CCC5)cc2)cc1 ; O=C([O-])C(F)(F)F]

Compound 7

Compound 7 is 16-[4-({[4-(aminomethyl)phenyl]methyl}carbamoyl)phenyl]-3-oxa-9$\lambda^5$,23-diazaheptacyclo [17.7.1.1$^{5,9}$.0$^{2,17}$.0$^{4,15}$.0$^{23,27}$.0$^{13,28}$]octacosa-1(27),2(17),4,9 (28),13,15,18-heptaen-9-ylium; 2,2,2-trifluoroacetate according to the nomenclature system that we use and is prepared using the same procedure as used for preparing Compound 3, but with [4-(aminomethyl)phenyl]methanamine replacing 1,2-diaminoethane (42 mg, 0.31 mmol) to obtain 36 mg (96% yield) product. Purity as determined by HPLC is 99%, MS (ESI) [M+]=609. Absorbance max is 590 nm.

Example 13: Preparation of a 4-carboxrhodamine trifluoroaceate (Compound 8)

The following compound is prepared:

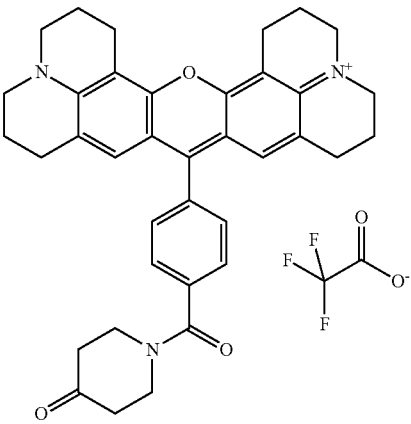 [SMILES: O=C1CCN(C(=O)c2ccc(C3=c4cc5c6c(c4Oc4c3cc3c7c4CCCN7CCC3)CCC[N+]=6CCC5)cc2)CC1 ; O=C([O-])C(F)(F)F]

Compound 8

Compound 8 is 16-{4-[(4-oxopiperidin-1-yl)carbonyl]phenyl}-3-oxa-9$\lambda^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; 2,2,2-trifluoroacetate according to the nomenclature system that we use and is prepared using the same procedure as used for Compound 3, but with piperidin-4-one replacing 1,2-diaminoethane (31 mg, 0.31 mmol) to obtain 28 mg (79% yield) product. Purity as determined by HPLC is 82%. MS (ESI) [M+]=572. Absorbance is max 588 nm.

Example 14: Preparation of a 3-carboxrhodamine trifluoroaceate (Compound 9)

The following compound is prepared:

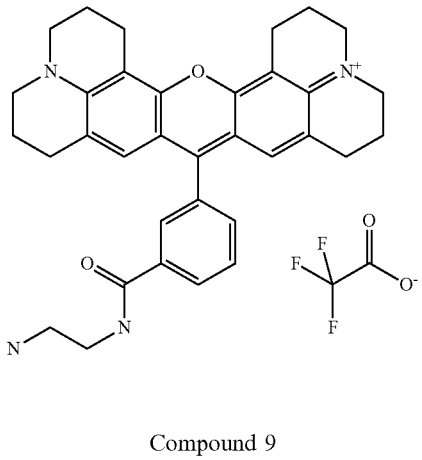

Compound 9

Compound 9 is 16-{3-[(2-aminoethyl)carbamoyl]phenyl}-3-oxa-9$\lambda^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; 2,2,2-trifluoroacetate according to the nomenclature system that we use and is prepared using the same procedure as used for Compound 3, but with Intermediate 3 replacing 1,2-diaminoethane as acid and 1,2-diaminoethane (19 mg, 0.31 mmol) as amine to obtain 20 mg (60% yield) product. Purity as determined by HPLC is 100%. MS (ESI) [M+]=533. Absorbance max is 586 nm.

Example 15: Preparation of a 3-carboxrhodamine trifluoroaceate (Compound 10)

The following compound is prepared:

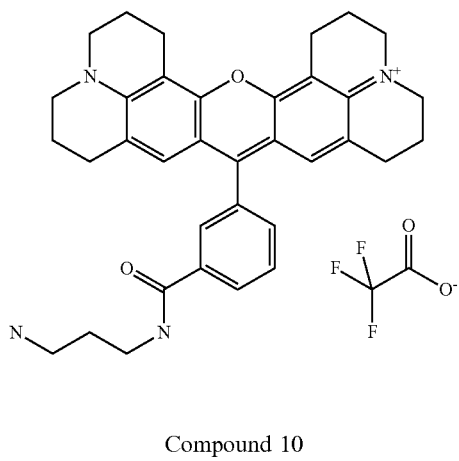

Compound 10

Compound 10 is 16-{3-[(3-aminopropyl)carbamoyl]phenyl}-3-oxa-9$\lambda^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; 2,2,2-trifluoroacetate according to the nomenclature system that we use and is prepared using the same procedure as used for preparing Compound 9, but with 1,3-diaminopropane replacing 1,2-diaminoethane (23 mg, 0.31 mmol) to obtain 19 mg (56% yield) product. Purity as determined by HPLC is 100%. MS (ESI) [M+]=547. Absorbance max is 584 nm.

Example 16: Preparation of a 3-carboxrhodamine trifluoroaceate (Compound 11)

The following compound is prepared:

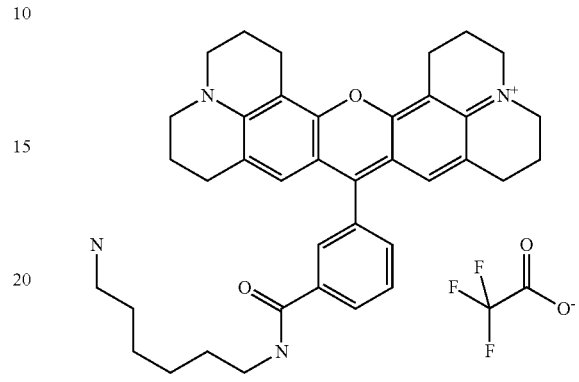

Compound 11

Compound 11 is 16-{3-[(6-aminohexyl)carbamoyl]phenyl}-3-oxa-9$\lambda^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; 2,2,2-trifluoroacetate according to the nomenclature system that we use and is prepared using the same procedure as used for preparing Compound 9, but with 1,6-diaminohexane replacing 1,2-diaminoethane (36 mg, 0.31 mmol) to obtain 27 mg (74% yield) product. Purity as determined by HPLC is 100%. MS (ESI) [M+]=589. Absorbance max is 584 nm.

Example 17: Preparation of a 3-carboxrhodamine trifluoroaceate (Compound 12)

The following compound is prepared:

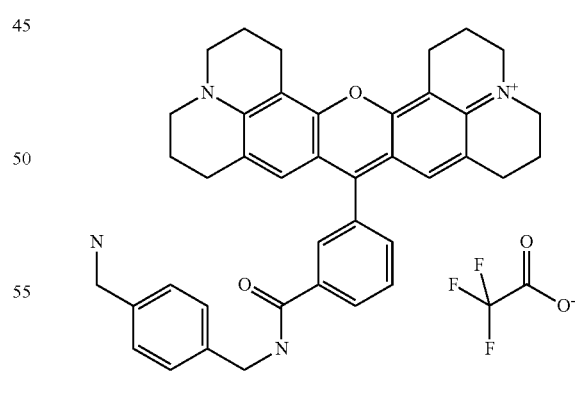

Compound 12

Compound 12 is 16-[3-({[4-(aminomethyl)phenyl]methyl}carbamoyl)phenyl]-3-oxa-9$\lambda^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; 2,2,2-trifluoroacetate according to the nomenclature system that we use and is prepared using the same procedure is as used for preparing Compound 9, but with [4-(aminomethyl)phenyl]methanamine replacing 1,2-diaminoethane (42 mg, 0.31 mmol) to obtain 32 mg (86% yield) product. Purity as determined by HPLC is 100%. MS (ESI) [M+]=609. Absorbance max is 587 nm.

Example 18: Preparation of a 3-carboxrhodamine trifluoroaceate (Compound 13)

The following compound is prepared:

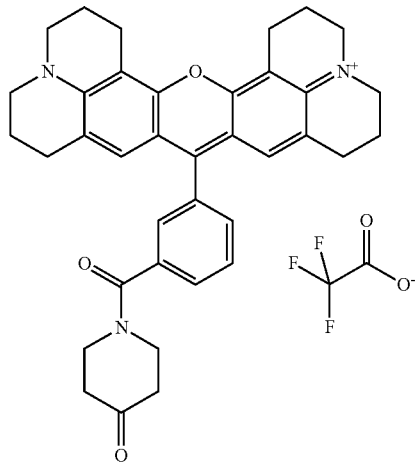 [SMILES: O=C1CCN(C(=O)c2cccc(C3=c4cc5c6c(c4Oc4c3cc3c7c4CCCN7CCC3)CCC[N+]=6CCC5)c2)CC1 ; O=C([O-])C(F)(F)F]

Compound 13

Compound 13 is 16-{3-[(4-oxopiperidin-1-yl)carbonyl]phenyl}-3-oxa-9λ$^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; 2,2,2-trifluoroacetate according to the nomenclature system that we rise and is prepared using the same procedure as used for preparing Compound 9, but with piperidin-4-one replacing 1,2-diaminoethane (31 mg, 0.31 mmol) to obtain 34 mg (96% yield) product. Purity as determined by HPLC is 80%). MS (ESI) [M+]=572. Absorbance max is 584 nm.

Example 19: Preparation of a 3-carboxrhodamine trifluoroaceate (Compound 14)

The following compound is prepared:

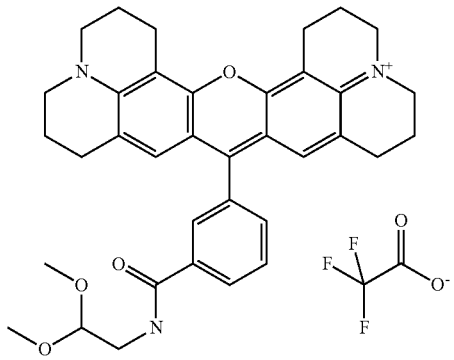 [SMILES: COC(CNC(=O)c1cccc(C2=c3cc4c5c(c3Oc3c2cc2c6c3CCCN6CCC2)CCC[N+]=5CCC4)c1)OC ; O=C([O-])C(F)(F)F]

Compound 14

Compound 14 is 16-{3-[(2,2-dimethoxyethyl)carbamoyl]phenyl}-3-oxa-9λ$^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; 2,2,2-trifluoroacetate according to the nomenclature system that we use and is prepared using the same procedure is as used for preparing Compound 9, but with 2,2-dimethoxyethan-1-amino replacing 1,2-diaminoethane (33 mg, 0.31 mmol) to obtain 29 mg (81% yield) product. Purity as determined by HPLC is 98%. MS (ESI) [M+]=578. Absorbance max is 588 nm.

Example 20: Preparation of a 4-carboxrhodamine trifluoroaceate (Compound 15)

The following compound is prepared:

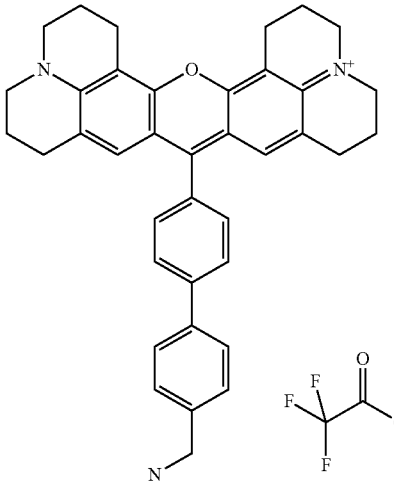

Compound 15

Compound 15 is 16-{4-[4-(aminomethyl)phenyl]phenyl}-3-oxa-9λ$^5$,23-diazaheptacyclo[17.7.1.1$^{5,9}$.0$^{2,17}$.0$^{4,15}$.0$^{23,27}$.0$^{13,28}$]octacosa-3(27),2(37),4,9(28),13,15,18-heptaen-9-ylium; 2,2,2-trifluoroacetate according to the nomenclature system that we use and is prepared as follows. Intermediate 5 (236 mg, 0.35 mmol) is dissolved in 4 mL DCM/TFA (3/1). After 30 minutes, the solvent is blown off with air. The crude product is purified on an ACE-C8 (150×30 mm) column eluting with 20-100% methanol in 0.1% TFA. Pure fractions are evaporated to 115 mg (% yield) deep blue/red solid with a green tinge. Purity as determined by HPLC is 98%. MS (ESI) [M+]=552. Absorbance max is 578 nm.

Example 21: Preparation of a 4-carboxrhodamine trifluoroaceate (Compound 16)

The following compound is prepared:

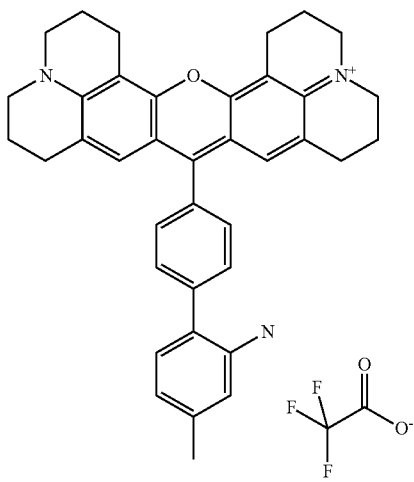 [SMILES: Cc1ccc(-c2ccc(C3=c4cc5c6c(c4Oc4c3cc3c7c4CCCN7CCC3)CCC[N+]=6CCC5)cc2)c(N)c1 ; O=C([O-])C(F)(F)F]

Compound 16

Compound 16 is 16-[4-(2-amino-4-methylphenyl)phenyl]-3-oxa-9λ$^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; 2,2,2-trifluoroacetate according to the nomenclature system that we use and is prepared as follows. Intermediate 4 (152 mg, 0.29 mmol) and 5-methyl-2-(4,4,5,5-tetramethyl)-(1,3,2-dioxaborolan-2-yl)-phenylamine (135 mg, 0.58 mmol) are dissolved in ethanol (10 mL) and treated with 2M K$_2$CO$_3$ (434 μL, 0.87 mmol) and [1,1'-bis(diphenylphosphino)ferrocene]dichloropalladium(II)DCM (11 mg, 0.015 mmol). The reaction mixture is heated at 65° C. for 1 hour. The crude product is filtered through celite and purified on an ACE-C8 (150×30 mm) column eluting with 60-100% methanol in 0.1% TFA, evaporating pure fractions to 80 mg (50% yield) deep blue/red solid with a green tinge. Purity as determined by HPLC is 90%. MS (ESI) [M+]=552. Absorbance max is 580 nm.

Example 22: Preparation of a 4-carboxrhodamine trifluoroaceate (Compound 17)

The following compound is prepared:

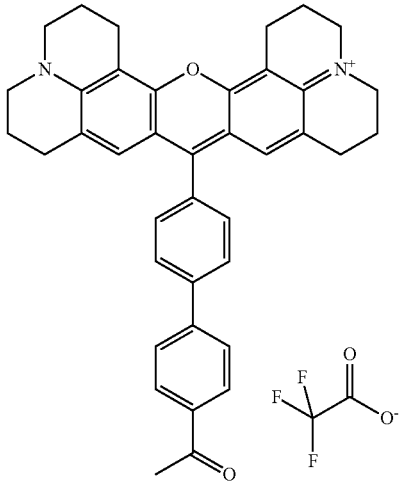 [SMILES: CC(=O)c1ccc(-c2ccc(C3=c4cc5c6c(c4Oc4c3cc3c7c4CCCN7CCC3)CCC[N+]=6CCC5)cc2)cc1 ; O=C([O-])C(F)(F)F]

Compound 17

Compound 17 is 16-[4-(4-acetylphenyl)phenyl]-3-oxa-9λ$^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; 2,2,2-trifluoroacetate according to the nomenclature system that we use and is prepared as follows. Intermediate 4 (152 mg, 0.29 mmol) and 4-ethanone phenyl boronic acid (95 mg, 0.58 mmol) are dissolved in ethanol (10 mL) and treated with 2M K$_2$CO$_3$ (434 μL, 0.87 mmol) and [1,1'-bis(diphenylphosphino)ferrocene]dichloropalladium(II), DCM (11 mg, 0.015 mmol). The reaction mixture is heated at 65° C. for 1 hour. The crude product is filtered through celite and purified on an ACE-C8 (150×30 mm) column eluting with 60-100% methanol in 0.1% TFA, evaporating pure fractions to 54 mg (33% yield) deep blue/red solid with a green tinge. Purity as determined by HPLC is 92%. MS (ESI) [M+]=565. Absorbance max is 580 nm.

Example 23: Preparation, Purification and Crystallization of a 2-sulforhodamine Dichloride (Compound 18)

The following compound is prepared:

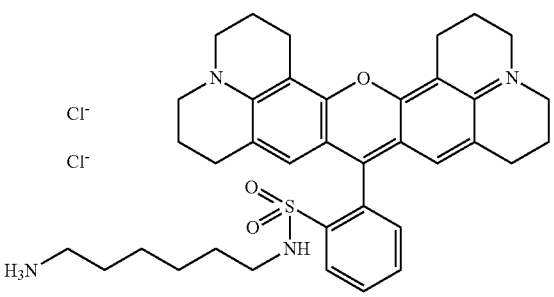

Compound 18

Compound 18 is 16-{2-[(6-aminohexyl)sulfamoyl]phenyl}-3-oxa-9$\lambda^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; dichloride according to the nomenclature system that we use and is prepared as follows.

Synthetic Step 1: A mixture of 8-hydroxyjulolidine (200 g) and sodium 2-formylbenzene-1-sulfonate (110 g) is added to 1.8 L of 60% H2SO4 aqueous pre-warmed at 150° C. and stirred for 4 hours. After the reaction is finished monitored by LC-MS, the reaction mixture is cooled to 0° C. 60% of sodium hydroxide (aqueous) is added slowly, until pH value of the reaction mixture to 2 (product is precipitated), Celite (800 g) is added to the reaction mixture with precipitated raw product and the reaction mixture is filtered. The resulting solid with celite is washed with toluene (3×500 mL) and added to anhydrous ethanol (4 L) and heated with stirring at 60° C. for 0.5 hour. The reaction mixture then is filtered. The filtrate is concentrated under vacuum and then co-evaporated with toluene to get rid of traces of water and to get crude Rhodamine sulfonic acid intermediate (270 g) as a dark blue solid.

Synthetic Step 2: Crude Rhodamine sulfonic acid intermediate from Step 1 (100 g, 0.19 mol) is dissolved in a mixture of solvents dichloromethane (500 mL) and DMF (13.9 g). The reaction solution is cooled to 0° C. and oxalyl chloride (48.1 g, 0.379 mol) is added dropwise. The reaction mixture is stirred for additional 2 hours at 0° C. The reaction mixture is then concentrated in vacuum and to the resulting residue is four iterations of adding toulene (100 mL) and evaporation performed. The crude Rhodamine sulfonic acid chloride intermediate is used directly in next step after drying under reduced pressure for 6 h.

Synthetic Step 3: A solution of hexane-1,6-diamine (176 g, 1.52 mol) in dichloromethane (800 mL) is cooled to 0° C. A solution of all crude Rhodamine sulfonic acid chloride intermediate obtained in Step 2 in dichloromethane (500 ml) is added dropwise with continued cooling to 0° C. The reaction mixture is stirred for an additional 4 hours at 0° C. After controlling with thin layer chromatography (TLC) that the reaction is complete, the reaction mixture is quenched by a filtration through celite-paper, and evaporating the filtrate in vacuum four times with additions of toluene (150 mL) each time. The resulting solid is dried under reduced pressure.

Purification: Purification by chromatography through silica gel is carried out using a mixture of solvents dichloromethane and MeOH (gradient from 15:1 to 1:1), saturated with HCl gas. A second silica gel chromatography yields 12.5 g of the 2-sulforhodamine dichloride (Compound 18) as a green-black solid (purity >98% by HPLC). The total yield for 3 all steps is 11.0%.

Crystallization: 2.5 g of the 2-sulforhodamine dichloride (Compound 18) of approx 88% purity is dissolved in ethanol (approx 50 mL) and ethyl acetate (approx. 150 mL) is added, which precipitates a sticky solid. The supernatant is treated with silica gel (5 g) and filtered. The silica is leached with 1 M HCl (200 mL), the resulting purple solution is then used to dissolve the sticky solid that is precipitated with ethyl acetate in a previous step. The solution is heated close to boiling and treated with warm brine (400 mL aq NaCl saturated at room temperature). The solution is allowed to cool to room temperature and minor precipitation is observed. pH is adjusted from −0.2 to +0.3 by careful addition of solid NaHCO3. The mixture is heated to boiling, a cooled aliquot of the solution is analyzed to pH 0.0. Solid NaHCO3 is added to the warm solution until a cooled sample showed pH 0.1. The suspension is allowed to cool to room temperature, alter two days the supernatant is analyzed to pH 0.0. Solid NaHCO3 is carefully added to the mixture without any more precipitation being observed (use a red lamp!). The solid is separated with centrifugation and the supernatant discarded (pH 0.0). The solid is suspended in the same volume of 20% aq NaCl that is used in the previous precipitation and centrifuged, discarding the supernatant (pH 0.5). The solid is again suspended in an equal volume, centrifuged and the supernatant discarded (pH 0.55). The second supernatant is not colorless and the washing procedure halted. The solid is dried in vacuum oven to 1.8 g of golden-green material, 96% purity with Syntagon's HPLC method. The above crystallization process can be used with an acetate salt of the 2-sulforhodamine (such as the trifluoroaceate salt as in Compound 1) instead of the dichloride salt of Compound 18.

Figure 6:
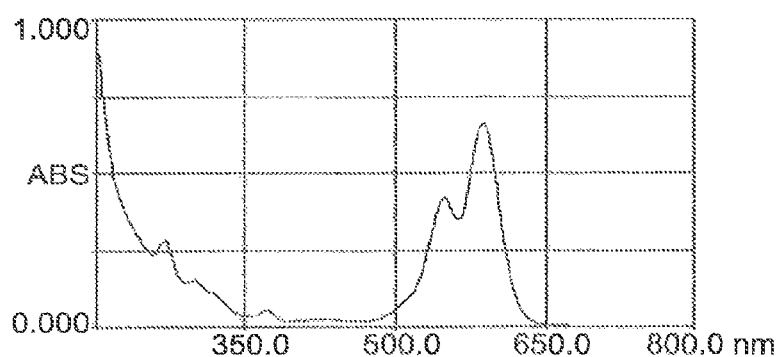
FIG. 6 is a UV absorption spectrum of Compound 18 scanning from 200 nm to 800 nm at a scan speed of 400 nm/minute.
Figure 7:
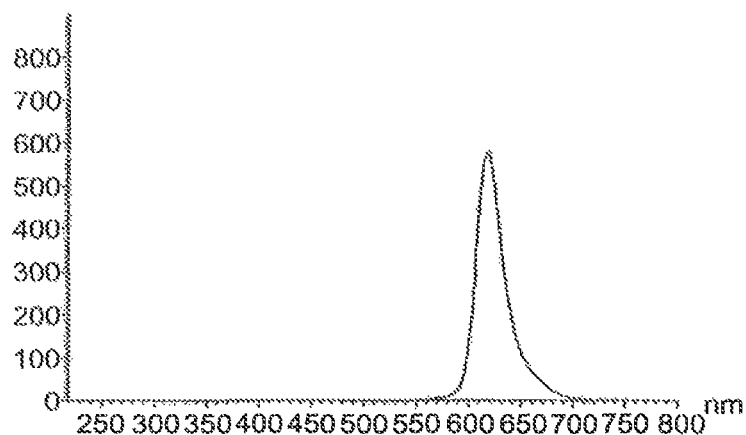
FIG. 7 is a fluorescence emission scan of Compound 18.
Figure 8:
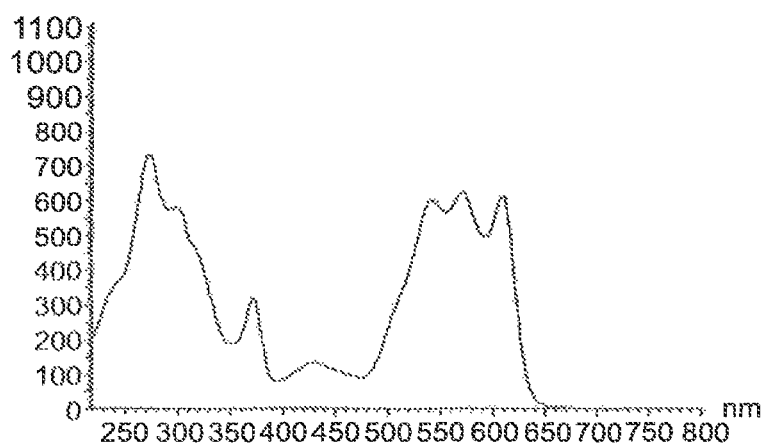
FIG. 8 is a fluorescence excitation scan of Compound 18.
Figure 9:
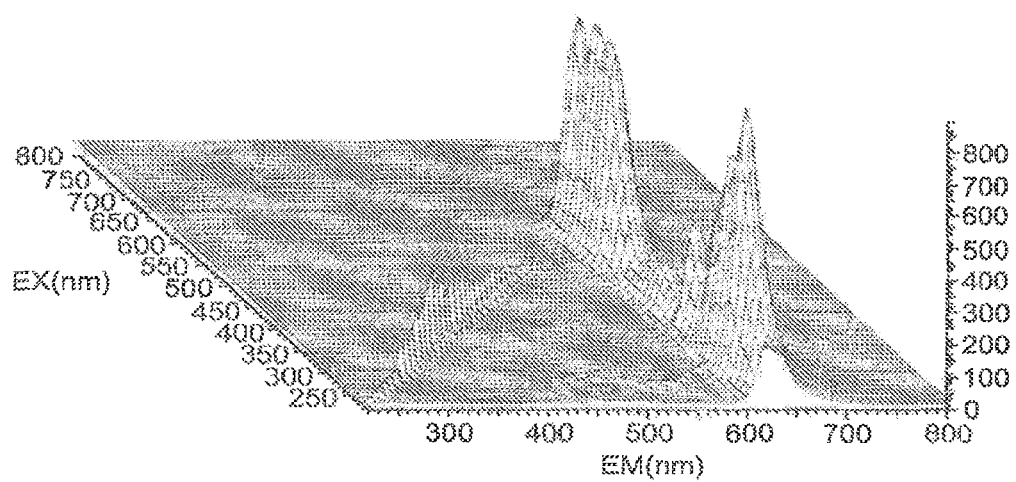
FIG. 9 is a 3-dimensional fluorescence scan of Compound 18 wherein EM is the emission wavelength and EX is the excitation wavelength.

FIG. 6 is a UV absorption spectrum of Compound 18 scanning from 200 nm to 800 nm at a scan speed of 400 nm/minute. The maximum UV absorption is at 586 nm. FIG. 7 is a fluorescence emission scan and FIG. 8 is a fluorescence excitation scan of Compound 18. FIG. 9 is a 3-dimensional fluorescence scan of Compound 18 wherein EM is the emission wavelength and EX is the excitation wavelength. The Excitation (max), which is the maximum absorbance wavelength, is 566 nm and the Emission (max), which is the wavelength with maximum emission intensity, is 618 nm.

Example 24: Rearrangement of Compound 18 to Form an Isomer (Compound 19)

The following compound is prepared;

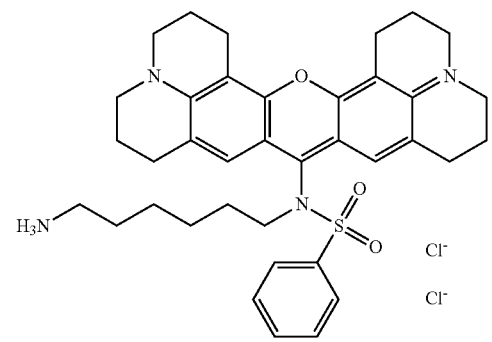

Compound 19

Compound 18 can undergo a re-arrangement to form an isomer Compound 19, which can be used like its parent compound Compound 18 and the other novel rhodamine dyes of the present invention in forming conjugates with other molecules, such as macromolecules, to form single isomeric conjugation products. Compound 19 is 16-[N-(6-azaniumylhexyl)benzenesulfonamido]-3-oxa-9$\lambda^5$,23-diazaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-9-ylium; dichloride according to the nomenclature system that we use and is prepared as follows. Compound 18 as the dichloride salt (1.16 g, 1.6 mmol) is dissolved in methanol (30 mL). Aqueous sodium hydroxide (1.0 M, 16 mL) is added dropwise to the 2-SHR solution at room temperature. The resulting colorless solution is stirred for 30 min at room temperature and then evaporated with ethanol (10 mL) and toluene (10 mL) to a colorless solid. The solid is dissolved in methanol (20 mL) and aqueous hydrochloric acid (1.0 M, 16 mL) is added, which reforms the deep red color. The mixture is evaporated and the solid residue purified with silica chromatography, eluting with methanol (10%-12.5%) in chloroform containing 0.1% concentrated hydrochloric acid. Selected pure fractions are evaporated with ethanol and toluene, drying at high vacuum overnight results in 120 mg 2-SHR-iso (11% yield) as a metallic green solid. Purity as determined by HPLC is 97.8%. MS (ESI) [M+]=625. Absorbance max is 586 nm.

Similarly, Compound 1 or any other salt of the 2-sulforhodamine can undergo the same re-arrangement as Compound 18 to form the corresponding isomeric product with the corresponding salt.

Example 25: Synthesis of Conjugate with Compound 15 and Carboxymethylated-Dextran (CM-Dextran)

To a solution of Compound 15 (Mw: 665.77 g/mol, n: 0.038 mmol, m: 25 mg) dissolved in dimethyl sulfoxide (DMSO) (3 ml) is added cold acetaldehyde from a stock solution (118 μl) with stirring. After 15 minutes a solution of CM-dextran 150 (300 mg) in distilled water (3 ml) is added with rapid stirring, followed by cyclohexyl-isonitrile (Mw: 109.1 g/mol, n: 0.21 mmol, m: 22.9 mg, δ: 0.878 g ml, V: 26.5 μl). The pH is adjusted to 5.9 with a few drops of 1M aq. HCl. The reaction mixture is left with stirring for four hours.

After four hours the pH has increased to 6.02. Ethanolamine (Mw: 61.08 g/mol, n: 3.34 mmol, m: 0,204 g, δ: 1.02, V: 200 μl) is added and the reaction is left for 90 minutes with stirring.

Ninety minutes after the addition of ethanolamine the pH has increased to 11.2. After addition of saturated sodium chloride (0.5 ml), the reaction mixture is slowly poured in to ethanol (96%, 50 ml) with rapid stirring where after the precipitated blue solid is allowed to settle overnight. The supernatant is decanted and the residue is filtered on a glass filter funnel (p3). The precipitate is washed with Ethanol (3×10 ml) and filtered. The product is reprecipitated until free from unreached dye. It is dried in vacuo at 60° C. for 15 hours. Yield is 225 mg.

Excitation (max) is 587 nm; Emission(max) is 608.

Example 26: Synthesis of Conjugate with Compound 18 with CM-Dextran

To a solution of Compound 18 (chloride salt, Mw: 697.7 g/mol, n: 0.136 mmol, m: 95.4 mg) dissolved in DMSO (14 mL) is added cold acetaldehyde from a stock solution (391 μL) with stirring. After 15 minutes a solution of CM-dextran 150 (1.8 g) in distilled water (19.2 mL) is added with rapid stirring, followed by cyclohexyl-isonitrile (Mw: 109.1 g/mol, n: 1.4 mmol, m: 152.6 mg, δ: 0.878 g/mL, V: 172 μl). The pH is adjusted to 5 with a few drops of 1M aq. HCl. The reaction mixture is left with stirring overnight.

Ethanolamine (Mw: 61.08 g/mol, n: 6.64 mmol, m: 0.40 g, δ: 1.02, V: 400 μL) is added and the reaction is left for 60 minutes with stirring.

Ninety minutes after the addition of ethanolamine the pH has increased to 11.2. After addition of saturated sodium chloride (0.5 ml), the reaction mixture is slowly poured hi to ethanol (96%, 50 ml) with rapid stirring where after the precipitated blue solid is allowed to settle overnight.

The supernatant is decanted and the residue is filtered on a glass filter funnel (p3). The precipitate is washed with ethanol (3×10 ml) and filtered. The product is reprecipitated until free from unreaeted dye. It is dried in vacuo at 60° C. for 15 hours. Yield is 1.3 g.

Figure 10:
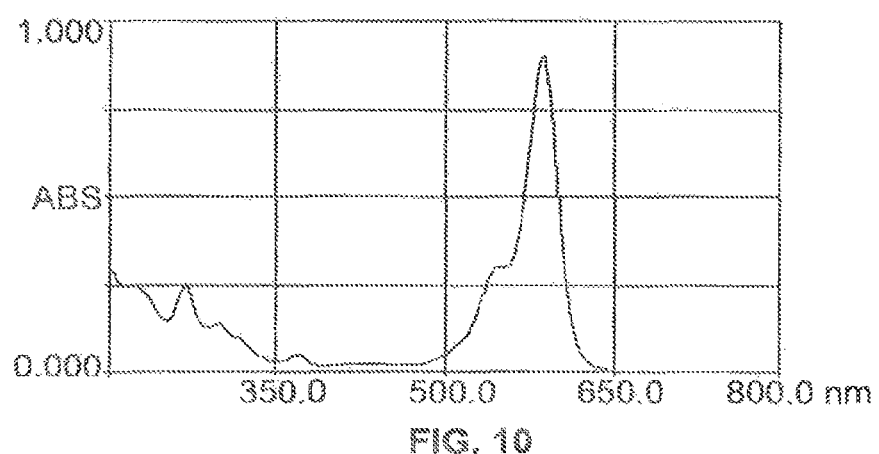
FIG. 10 is a UV absorption spectrum of the conjugate of Example 26 scanning from 200 nm to 800 nm at a scan speed of 400 nm/minute.
Figure 11:
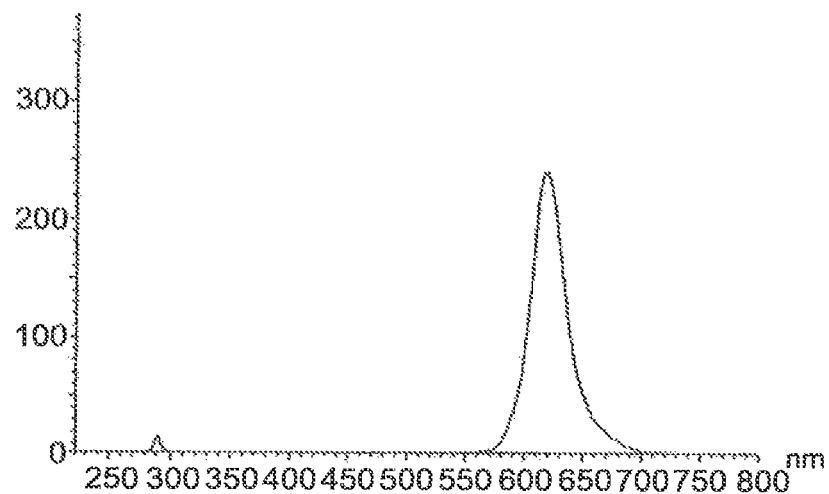
FIG. 11 is a fluorescence emission scan of the conjugate of Example 26.
Figure 12:
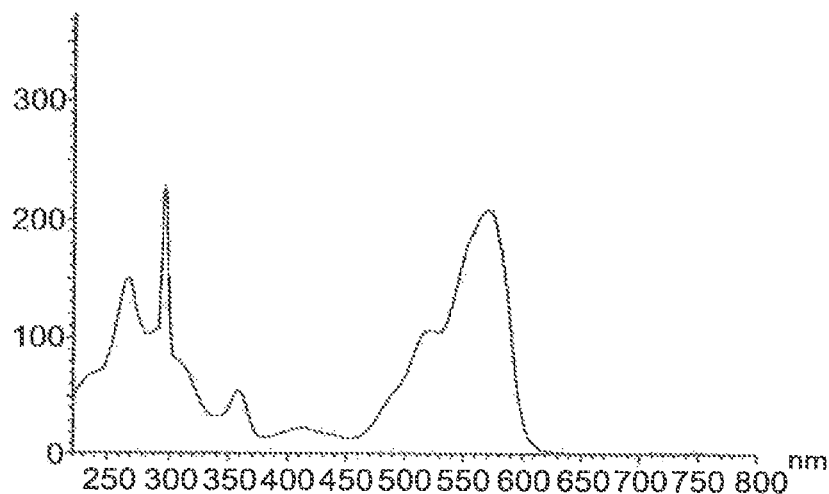
FIG. 12 is a fluorescence excitation scan of the conjugate of Example 26.
Figure 13:
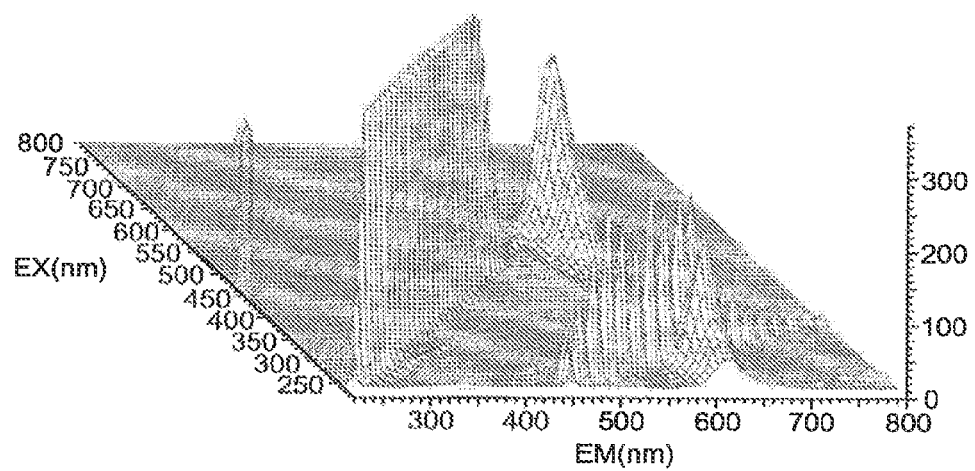
FIG. 13 is a 3-dimensional fluorescence scan of the conjugate of Example 26 wherein EM is the emission wavelength and EX is the excitation wavelength.

FIG. 10 is a UV absorption spectrum of the conjugate scanning from 200 nm to 800 nm at a scan speed of 400 nm/minute. The maximum UV absorption is at 589.5 nm. FIG. 11 is a fluorescence emission scan and FIG. 12 is a fluorescence excitation scan of the conjugate. FIG. 13 is a 3-dimensional fluorescence scan of the conjugate wherein EM is the emission wavelength and EX is the excitation wavelength.

Excitation (max) is 589 nm; Emission(max) is 608 nm.

Example 27: Synthesis of Conjugate with Compound 3 with CM-Dextran

To a solution of Compound 3 (TFA salt, Mw: 646.7 g/mol, n: 0.037 mmol, m: 24 mg) dissolved in DMSO (3 mL) is added cold acetaldehyde from a stock solution (118 μL) with stirring. After 15 minutes a solution of CM-dextran 150 (300 mg) in distilled water (3 mL) is added with rapid stirring, followed by cyclohexyl-isonitrile (Mw: 109.1 g/mol, n: 0.21 mmol, m: 22.9 mg, δ: 0.878 g/mL, V: 26.5 μL). The pH is adjusted to 5 with a few drops of 1M aq. HCl. The reaction mixture is left with stirring for 4 hours.

Ethanolamine (Mw; 61.08 g/mol, n: 6.64 mmol, m: 0.20 g, δ: 1.02, V: 200 μL) is added and the reaction is left for 60 minutes with stirring. The reaction product, after addition of saturated sodium chloride (0.5 ml), is slowly poured into ethanol (96%, 50 ml) with rapid stirring whereafter the precipitated blue solid is allowed to settle overnight.

The supernatant is decanted and the residue is filtered on a glass filter funnel (p3). Tire precipitate is washed with ethanol (3×10 ml) and filtered. The product is reprecipitated until free from unreaeted dye. It is dried in vacuo at 60° C. for 15 hours. Yield is 339 mg.

Excitation (max) is 588 nm; Emission(max) is 609 nm.

Example 28: Synthesis of Conjugate with Compound 16 with CM-Dextran

To a solution of Compound 16 (TFA salt, Mw: 665.7 g/mol, n: 0.038 mmol, m: 25 mg) dissolved in DMSO (3 mL) is added cold acetaldehyde from a stock solution (118 μL) with stirring. After 15 minutes a solution of CM-dextran 150 (300 mg) in distilled water (3 mL) is added with rapid stirring, followed by cyclohexyl-isonitrile (Mw: 109.1 g/mol, n: 0.21 mmol, m: 22.9 mg, δ: 0.878 g/mL, V: 26.5 μL). The pH is adjusted to 5 with a few drops of 1M aq. HCl. The reaction mixture is left with stirring for 4 hours.

Ethanolamine (Mw: 61.08 g/mol, n: 6.64 mmol, m: 0.20 g, δ: 1.02, V: 200 μL) is added and the reaction is left for 60 minutes with stirring. The reaction product, after addition of saturated sodium chloride (0.5 ml), is slowly poured into ethanol (96%, 50 ml) with rapid stirring where after the precipitated blue solid is allowed to settle overnight. The supernatant is decanted and the residue is filtered on a glass filter funnel (p3). The precipitate is washed with ethanol (3×10 ml) and filtered. The product is reprecipitated until free from unreacted dye. It is dried in vacuo at 60° C. for 15 hours. Yield is 167 mg.

Excitation (max) is 585 nm; Emission(max) is 606 nm.

REFERENCES

1. Lee S, McAuliffe D J, Kodama T, Doukas A G, in vivo transdermal delivery using a shock tube, Shock Waves (2000) 10:307-307
2. Janson L W, Ragsdale K, Luby-Phelps K, Mechanism and size cutoff for steric exclusion from actin-rich cytoplasmic domains., Biophys J (1996) 71:1228-1234
3. Pu R, Robinson K R, Cytoplasmic calcium gradients and calmodulin in the early development of the fucoid alga Pelvetia compressa., J Cell Sci (1998) 111 (Pt 21):3197-3207
4. Nishiya T, Kajita E, Horinouchi T, Nishimoto A, Miwa S, Distinct roles of TIR and non-TIR regions in the subcellular localization and signaling properties of MyD88, FEBS Lett (2007) 581:3223-3229
5. Tanner G A, Sandoval R M, Dunn K W, Two-photon in vivo microscopy of sulfonefluorescein secretion in normal and cystic rat kidneys, Am J Physiol Renal Physiol (2004) 286:F152-F160
6. Titus J A, Haugland R, Sharrow S O, Segal D M, Texas Red, a hydrophilic, red-emitting fluorophore for use with fluorescein in dual parameter flow microfluorometric and fluorescence microscopic studies, J. Immunol. Methods (1982) 50 (2): 193-204
7. Nimmerjahn, A., Kirchhoff, F., Kerr, J. N., Helmchen, F., Sulforhodamine 101 as a specific marker of astroglia in the neocortex in vivo. Nature Methods (2004) 1:31-7
8. Kim, T. G.; Castro, J. C.; Loudet, A.; Jiao, I. G.-S.; Hochstrasser, R. M.; Burgess, K.; Topp, M. R., Journal of Physical Chemistry A (2006), 110(1), 20-27

We claim:

1. A compound comprising a rhodamine dye or a salt thereof having the general structure of

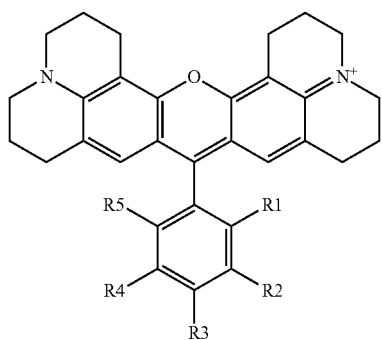

having a single functional group wherein the R1, R2, R3, R4 and R5 groups are independently selected as follows:
R5 is independently H
R4 is independently H or

R3 is independently H,

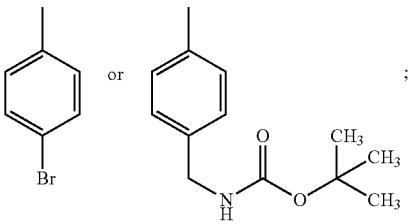

R2 is independently H or

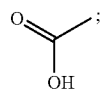

and R1 is H.

2. The compound of claim 1, wherein the salt is a pharmaceutically acceptable salt.

3. The compound of claim 2, wherein the salt is selected from the group consisting of trifluoroacetate, chloride, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate and p-toluenesulfonate.

4. The compound of claim 3, wherein the salt is chloorride.

5. A method of making the compound of claim 1, wherein R1, R3, and R5 are H, R2 is H or

and R4 is H or

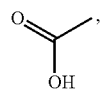

the method comprising the steps of:
mixing 8-hydroxyjulolidine and 3-formyl benzoic acid in aqueous $H_2SO_4$.

6. A method of making the compound of claim 1, wherein R1, R2, R4 and R5 are H and R3 is

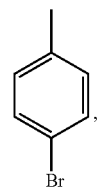

the method comprising the steps of:
mixing 8-hydroxyjulolidine and 4-bromobenzaldehyde in aqueous H₂SO₄.

7. A method of making the compound of claim 1, wherein R1, R2, R4 and R5 are H and R3 is

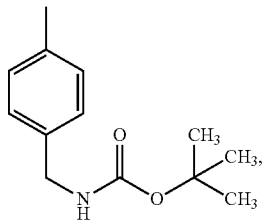 [SMILES: Cc1ccc(CNC(=O)OC(C)(C)C)cc1]

the method comprising the steps of:
preparing a reaction mixture comprising the compound of claim 1 wherein R1, R2, R4 and R5 are H and R3 is

and tert-butyl N-{[4-(dihydroxyboranyl)phenyl]methyl}carbamate in an aqueous solution of ethanol and K₂CO₃;

degassing said reaction mixture; and adding [1,1'-bis(diphenylphosphino)ferrocene]dichloropalladium(II).

8. A method of using the compound of claim 1, wherein R1, R3, and R5 are H, R2 is H or

and R4 is H or

for making a rhodamine dye or a salt thereof having the general structure of

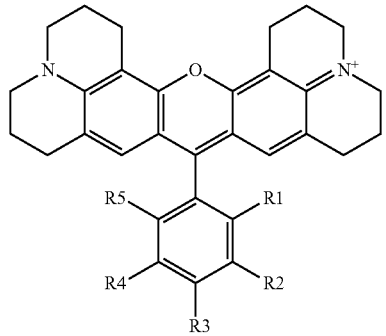

wherein R1, R3, and R5 are H, R2 is H or

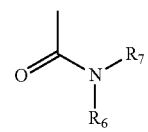

and R4 is H or

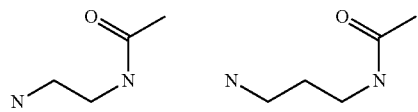

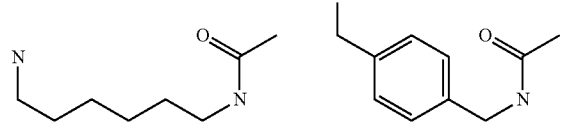

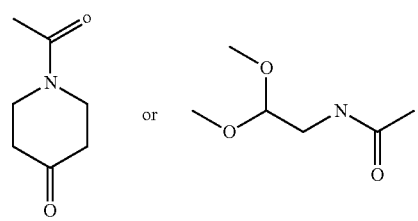

wherein the R6 and/or R7 form a spacer which contains a single functional group, said method comprising the steps of:

dissolving said compound of claim 1 in DMF-CH₃CN to form a solution;

preparing a reaction mixture by adding triethylamine and 2,4,6-tripropyl-1,3,5,2,4,6-trioxatriphosphorinane-2,4,6-trioxide in ethyl acetate to the solution; and adding the reaction mixture to 1,2-diaminoethane, 1,3-diaminopropane, 1,6-diaminohexane, [4-(aminomethyl)phenyl]methanamine, piperidin-4-one or 2,2-dimethoxyethan-1-amine.

9. A method of using the compound of claim 1, wherein R1, R2, R4 and R5 are H and R3 is

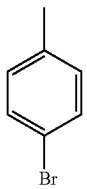

for making a rhodamine dye or a salt thereof having the general structure of

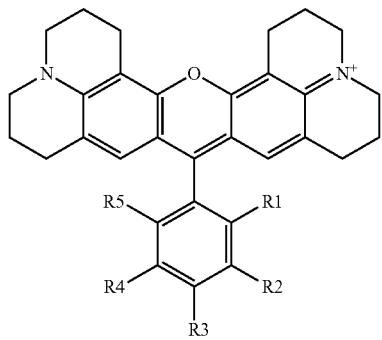

wherein R1, R2, R4 and R5 are H and R3 is

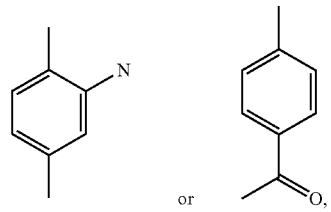

said method comprising the steps of:
 dissolving said compound of claim 1 and 5-methyl-2-(4,4,5,5-tetramethyl)-1,3,2-dioxaborolan-2-yl)-phenylamine or 4-ethanone phenyl boronic acid in ethanol to form a solution;
 preparing a reaction mixture by adding K₂CO₃ and [1,1'-bis(diphenylphosphino)ferrocene]dichloropalladium (II)DCM to the solution; and
 heating.

10. A method of using the compound of claim 1, wherein R1, R2, R4 and R5 are H and R3 is

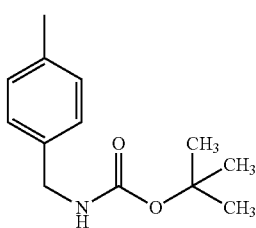 [SMILES: Cc1ccc(CNC(=O)OC(C)(C)C)cc1]

for making a rhodamine dye or a salt thereof having the general structure of

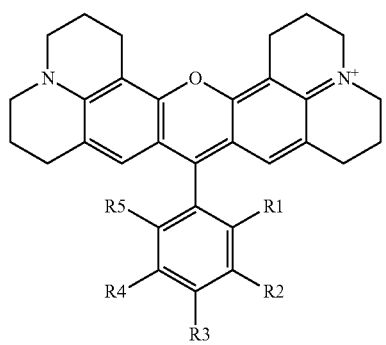

wherein R1, R2, R4 and R5 are H and R3 is

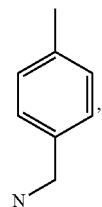

said method comprising the steps of:
 dissolving said compound of claim 1 in DCM/TFA.

* * * * *